(12) United States Patent
Jellus et al.

(10) Patent No.: US 8,917,918 B2
(45) Date of Patent: Dec. 23, 2014

(54) METHOD TO GENERATE MAGNETIC RESONANCE SLICE EXPOSURES

(71) Applicants: Vladimir Jellus, Kirchehrenbach (DE); Mathias Nittka, Baiersdorf (DE)

(72) Inventors: Vladimir Jellus, Kirchehrenbach (DE); Mathias Nittka, Baiersdorf (DE)

(73) Assignee: Siemens Aktiengesellschaft, Munich (DE)

( * ) Notice: Subject to any disclaimer, the term of this patent is extended or adjusted under 35 U.S.C. 154(b) by 120 days.

(21) Appl. No.: 13/782,256

(22) Filed: Mar. 1, 2013

(65) Prior Publication Data

US 2013/0230223 A1    Sep. 5, 2013

(30) Foreign Application Priority Data

Mar. 2, 2012 (DE) .......................... 10 2012 203 288

(51) Int. Cl.
| | |
|---|---|
| *G06K 9/00* | (2006.01) |
| *G01R 33/565* | (2006.01) |
| *A61B 5/00* | (2006.01) |
| *A61B 5/055* | (2006.01) |
| *G01R 33/48* | (2006.01) |
| *G01R 33/483* | (2006.01) |

(52) U.S. Cl.
CPC .......... *G01R 33/56527* (2013.01); *A61B 5/00* (2013.01); *A61B 5/055* (2013.01); *A61B 5/4872* (2013.01); *A61B 5/4875* (2013.01); *G01R 33/4828* (2013.01); *G01R 33/4835* (2013.01)
USPC ................... 382/128; 378/1; 600/410

(58) Field of Classification Search
None
See application file for complete search history.

(56) References Cited

U.S. PATENT DOCUMENTS

| | | | | |
|---|---|---|---|---|
| 4,993,075 | A * | 2/1991 | Sekihara et al. ............... | 382/131 |
| 5,546,472 | A * | 8/1996 | Levin ............................. | 382/131 |
| 6,070,095 | A * | 5/2000 | McKinnon et al. ........... | 600/410 |
| 6,714,807 | B2 * | 3/2004 | Zur ................................ | 600/410 |
| 6,819,952 | B2 * | 11/2004 | Pfefferbaum et al. ........ | 600/410 |
| 7,099,499 | B2 * | 8/2006 | Blezek et al. ................. | 382/128 |
| 7,257,244 | B2 * | 8/2007 | Miga ............................. | 382/128 |
| 7,649,353 | B2 * | 1/2010 | Feiweier et al. .............. | 324/309 |
| 7,676,075 | B2 * | 3/2010 | Smith et al. ................... | 382/131 |
| 7,787,676 | B2 * | 8/2010 | Drobnitzky ................... | 382/128 |
| 8,072,466 | B2 * | 12/2011 | Harder et al. ................. | 345/619 |

OTHER PUBLICATIONS

Yu et al. "implementation and Noise Analysis of Chemical Shift Correction for Fast Spin Echo Dixon Imaging," Proc Intl Soc. Mag. reson. Med 11 (2004) p. 2686.

(Continued)

*Primary Examiner* — Manav Seth
(74) *Attorney, Agent, or Firm* — Schiff Hardin LLP (57) ABSTRACT

In a method processor and magnetic resonance (MR) system to generate MR slice exposures of an examination subject, measurement data for a stack of measurement slices through the examination subject are initially acquired using a series of slice measurement sequences. The series of slice measurement sequences is designed to allow a separation of a first material from a second material that has a defined chemical shift relative to said first material, and the position of a measurement slice with measurement data for the first material is spatially shifted relative to the position of a measurement slice with measurement data for the second material. Combination slice exposures are then formed by combining measurement data of the first material from at least a first slice measurement sequence with measurement data of the second material from at least one second slice measurement sequence, such that the image data of the first and second materials are spatially arranged with precise positioning relative to one another, at least within a predetermined degree of tolerance in the combination slice exposures.

14 Claims, 5 Drawing Sheets

(56) References Cited

OTHER PUBLICATIONS

Ivanov et al. "A simple Low-SAR Technigue for Chemical-Shift Selection with High-Field Sping-Echo Imaging," Magnetic Resonance in Medicine, vol. 64, pp. 319-326 (2010).

Leinhard et al. "Water fat shift displacement artifact correction in two pioint Dixon imaging," Proc. Intl. Soc. Mag. Reson. Med. vol. 16, p. 1384 (2008).

Kwok et al. "Interleaved Water and Fat Dual-Echo Spin Echo Imaging With Intrinsic Chemical-Shift Elimination," J. Magn. Reson. Imaging, vol. 13, pp. 318-323 (2001).

Lu et al., "Water-Fat Separation with Bipolar Multiecho Sequences,". Mag. Reson. Med. vol. 60, pp. 198-209 (2008).

Romu et al., "Fat Water Classification of Symmetrically Sampled Two-Point Dixon Using Biased Partial Volume Effects," Proc. Intl. Soc. Mag. Reson. Med. vol. 19, p. 2711, (2011).

Nittka et al., "Through-Plane Chemical shift Correction in Rf-Power Reduced Sequences at High Field Strength," ISMRM Konferenz (2012).

* cited by examiner

METHOD TO GENERATE MAGNETIC RESONANCE SLICE EXPOSURES

BACKGROUND OF THE INVENTION

1. Field of the Invention

The invention concerns a method to generate magnetic resonance (MR) slice exposures of an examination subject, as well as an MR measurement data processing unit to generate MR slice exposures, and an MR system that, among other things, has such an MR measurement data processing unit.

2. Description of the Prior Art

In order to obtain magnetic resonance slice exposures (i.e. image data generated with a magnetic resonance tomograph apparatus) from a region of the inside of the body of an examination subject, the body or the body part to be examined must initially be exposed to an optimally homogeneous, static basic magnetic field, which is most often designated as a $B_0$ field. The nuclear spins in the body are thereby aligned parallel to the direction of the $B_0$ field (typically designated as the z-direction of a Cartesian coordinate system). Moreover, radio-frequency pulses (RF pulses) having a frequency in the range of the resonance frequency (known as the Larmor frequency) of the nuclei to be excited in the present $B_0$ field, are radiated into the examination subject with suitable radio-frequency antennas. The spins of the nuclei to be excited—normally hydrogen nuclei since water is abundantly present in the body—in the examination subject are excited by these radio-frequency pulses such that they are deflected out of their rest state, parallel to the basic magnetic field $B_0$, by an amount known as the "excitation flip angle." The excited nuclear spins then initially precess around the z-direction and relax again bit by bit, the relaxation being dependent on the chemical shift and the molecular environment in which the excited nucleus is located. The magnetic resonance signals generated upon relaxation are acquired as raw data by radio-frequency reception antennas, and the magnetic resonance images are ultimately reconstructed on the basis of the acquired raw data. Spatial coding takes place with the use of rapidly switched gradient magnetic fields that are superimposed on the basic magnetic field $B_0$ during the emission of the magnetic resonance radio-frequency pulses and/or the acquisition of the raw data.

Typical magnetic resonance imaging is based on the sequential excitation and readout of arbitrarily oriented slices in the examination subject. In order to cover a three-dimensional volume of a specific volume known as a "region of interest" (ROI), measurement data (raw data) are typically generated by means of a succession of slice measurement sequences in order to obtain a complete stack of parallel measurement slices through the examination subject that are spatially shifted relative to one another in a defined stack direction (for example in the z-direction). This slice stack can be constructed so that one slice immediately adjoins the next slice, such that the volume is seamlessly covered. However, it is also possible to acquire the slices with a determined slice interval. The defined excitation of a slice can take place by radiating a radio-frequency pulse with simultaneous application of a slice selection gradient in the stack direction, for example in the z-direction. The thickness of the selected slice is determined by the bandwidth of the RF pulse as well as the amplitude of the slice selection gradient; the slice position is determined by the Larmor frequency present at the respective location, which Larmor frequency is dependent on the magnetic field $B_0$ that is present at the respective location.

In this typically used type of slice excitation, the problem exists that the excited nuclei in the body tissue have no uniform precession frequency in the magnetic field; rather, they can differ according to their chemical environment for different tissue types. This is typically designated as a chemical shift. In magnetic resonance imaging, the chemical shift of fat tissue in relation to the typically excited hydrogen nuclei of water is particularly interfering, since fat occurs in significant quantities in many body regions. The chemical shift between fat tissue and water amounts to approximately 3.5 ppm. Upon slice excitation, the effect of the chemical shift has the effect that the signal of tissue with deviating frequency is shifted in the stack direction. In the extreme case, this can lead to the situation that the fat signal in the image data generated from the raw data originates from a completely different slice position, and thus contrasts and anatomy are adulterated in the diagnostic image generated later from this image data.

This problem intensifies with increasing field strength of the $B_0$ field, for two reasons. The slice offset increases proportionally with the field strength. For example, given a slice thickness of 3 mm and a bandwidth of the exciting RF pulse of 1 kHz, at a field strength of 1.5 Tesla the fat signal is shifted by approximately 0.63 mm (which constitutes approximately 23% of the slice thickness) relative to the water signal. At 3 Tesla, this shift doubles relative to a 1.5 Tesla magnetic field, meaning that it then amounts to 1.26 mm (which makes up 42% of the slice thickness). At 7 Tesla, the distance already amounts to 2.98 mm (which constitutes 98% of the slice thickness). While the shift thus appears to still be acceptable give routine examinations at 1.5 Tesla systems, the fat signal at 7 Tesla systems already originates from a completely different slice position, which can lead to significant problems in the later diagnostic evaluation.

An additional reason why the problem intensifies with increasing magnetic field strength is that, at higher field strengths, radio-frequency pulses with lower bandwidth should be used in order to reduce the radio-frequency exposure of the patient, known as the SAR (specific absorption rate). Although the use of RF pulses with lower bandwidth is counterproductive for image artifacts that occur due to the chemical shift, this is nevertheless frequently done in order to avoid otherwise necessary SAR limitations.

SUMMARY OF THE INVENTION

An object of the present invention to provide a method to generate magnetic resonance slice exposures, as well as a measurement data processing unit that is suitable for this purpose, with which method and processing unit artifacts due to the chemical shift in the stack direction can be reduced, and even be completely avoided in the most advantageous case.

In the method according to the invention, the magnetic resonance system is initially activated by a series of slice measurement sequences so that measurement data are generated for a stack of measurement slices though the examination subject. As used herein, measurement data of a measurement slice are both the raw data acquired for this measurement slice and the image data of this slice that are reconstructed from the raw data.

The individual measurement slices of this stack are spatially shifted counter to one another in a defined stack direction (preferably in the z-direction, i.e. the direction of the z-gradient) and are preferably parallel. The stack direction is the direction that projects out of the image plane, i.e. it is at a non-zero degree angle, preferably orthogonal, to the slice plane, and along which the successive measurement slices are arranged next to one another. According to the invention, the sequence (succession) of slice measurement sequences is designed or configured so that it allows a separation of a first material from a second material that has a defined chemical shift relative to the first material, and the position of a measurement slice with measurement data for the first material is thereby spatially shifted relative to the position of a measurement slice with measurement data for the second material.

A slice is associated with each slice measurement sequence of the series of slice measurement sequences. The series of radio-frequency pulses and gradient pulses as well as a corresponding readout of the raw data for the appertaining measurement slice is used herein as meaning a "slice measurement sequence." As is explained below, it is possible within the scope of the invention to use slice measurement sequences that simultaneously acquire one measurement slice with measurement data for the first material and a measurement slice shifted relative to this with measurement data for the second material. Alternatively, series of slice measurement sequences can be used in which the measurement slices are acquired for the first material and the second material respectively in separate slice measurement sequences.

According to the invention, a combination slice exposures in which the first and second material are respectively shown is then subsequently formulated on the basis of the generated measurement data. Measurement data of the first material from at least one first measurement slice are thereby combined with measurement data of the second material from at least one second measurement slice that is shifted relative to the first measurement slice, such that the image data of the first material and second material in the combination slice exposures are spatially arranged with precise position relative to one another, at least within a predetermined degree of tolerance. A positionally precise, correct association within a predetermined degree of tolerance means that the positions correspond as exactly as possible to the real spatial position of the material, and the deviation preferably amounts to at most 50%, and more preferably at most 25%, and most preferably at most 10% of the slice thickness. This means that the degree of tolerance is selected so that diagnostically relevant artifacts due to the shift are no longer present in the combination slice exposures.

With the method according to the invention, using otherwise typical measurement methods it is possible to generate slice images without generating artifacts caused by a chemical shift in the stack direction, even when only low radio-frequency bandwidths are used and thus the radio-frequency exposure for the patient is reduced. This primarily also applies in radio-frequency magnetic systems of 3 Tesla or more. It is thus also possible to not have to generate fat-suppressed images within the scope of turbo spin echo sequences (TSE sequences). Such TSE sequences are of high importance for routine imaging due to their broad spectrum of clinical contrast (primarily weighting of the proton density, T1 and T2 relaxation) as well as a relative interference-insensitivity with regard to local magnetic field inhomogeneities. However, due to a short time sequence of radio-frequency pulses with high flip angle, such TSE sequences can cause a relatively high radio-frequency exposure for the patient, such that the pulse bandwidth must be severely reduced given high-field MR systems, which in turn has previously led to significant artifacts without the solution according to the invention.

A measurement data processing unit according to the invention for the generation of magnetic resonance slice exposures of an examination subject requires a measurement data interface to accept measurement data generated by a series of slice measurement sequences for a stack of measurement slices through the examination subject, wherein the measurement data include at least measurement data of a first material and a second material that has a defined chemical shift relative to the first material, and the position of a measurement slice with measurement data for the first material is spatially shifted relative to the position of a measurement slice with measurement data for the second material.

The measurement data processing unit according to the invention also requires a measurement data combination unit that generates combination slice exposures on the basis of the measurement data, in which combination slice exposures the first and second material are respectively shown, wherein measurement data of the first material from at least one first measurement slice are combined with measurement data of the second material from at least one second measurement slice, such that the image data of the first and second material in the combination magnetic resonance exposures are spatially arranged with positional precision relative to one another (within a predetermined degree of tolerance) in the combination magnetic resonance exposures.

A magnetic resonance system according to the invention includes the following components:

a basic field magnet system that applies a homogeneous basic magnetic field in a measurement space in which the examination subject is located, an RF transmission antenna system that emits radio-frequency pulses into the examination subject, a gradient system that emits gradient pulses as described above, and an RF reception antenna system that detects the magnetic resonance signals from the examination subject. The RF transmission antenna system and the RF reception antenna system can be different antenna systems, or the same antenna system.

Furthermore, the magnetic resonance system requires a control device that—in the operation to generate magnetic resonance slice exposures of an examination subject—activates the basic field magnet system, the RF transmission antenna system, the gradient system and the RF reception antenna system such that measurement data for a stack of measurement slices through the examination subject are generated by means of a series of slice measurement sequences, wherein (as described above) the series of slice measurement sequences is constructed so that it allows a separation of a first material from a second material which has a defined chemical shift relative to said first material, and the position of a measurement slice with measurement data for the first material is spatially shifted relative to the position of a measurement slice with measurement data for the second material.

For example, for this purpose the control device can have various sub-components such as a radio-frequency transmission device to send radio-frequency pulses to the RF transmission antenna system; a gradient system interface to control the gradient system; a radio-frequency reception device to receive raw data via the RF reception antenna system; and a sequence control unit that conveys measurement sequence control data to the radio-frequency transmission device, the gradient system interface and the radio-frequency reception device to generate the magnetic resonance exposures upon operation, such that (as previously described) these said measurement sequence control data control the basic field magnet system, the RF transmission antenna system, the gradient system and the RF reception antenna system in the manner according to the invention to generate the measurement data for a stack of measurement slices.

Furthermore, the magnetic resonance system requires a measurement data processing unit according to the invention that generates the combination slice exposures on the basis of measurement data, as described above.

The measurement data processing unit does not necessarily need to be an immediate part of the magnetic resonance system; rather, it is possible to displace the combination of the measurement data according to the invention to an external measurement data processing unit which, for example, is located in a computer system purely for reconstruction of the image data from the raw data or in a finding workstation in order to thus keep the computing capacities of the magnetic resonance system themselves free for additional, subsequent measurements.

The measurement data processing unit and/or the sequence control unit can preferably be realized in the form of software at a suitable programmable control device with corresponding memory capabilities. The radio-frequency transmission device, the gradient system interface and the radio-frequency reception device can also be realized at least partially in the form of software units, wherein other units of these components are in turn purely hardware units, for example the radio-frequency amplifier, the radio-frequency transmission device, a gradient pulse generation device of the gradient system interface or an analog/digital converter of the radio-frequency reception device etc. A realization largely in software—in particular of the sequence control unit—has the advantage that even previously used magnetic resonance system control devices can also be upgraded in a simple manner via a software update in order to operate in the manner according to the invention.

Therefore, the above object is also achieved by a non-transitory, computer-readable data storage medium encoded with programming instructions. The storage medium can be a portable memory and/or be formed transmission of the programming instructions via a network directly into a memory of a programmable magnetic resonance system control device and/or measurement data processing unit, with program segments in order to execute all steps of the method according to the invention when the program is executed in the control devices and/or the measurement data processing unit.

The advantages discussed above that are achieved by the method in accordance with the invention are likewise achieved by the processor, the magnetic resonance imaging system, and the non-transitory, computer-readable data storage medium in accordance with the invention.

The method according to the invention is in principle applicable for arbitrary materials that exhibit a chemical shift relative to one another, for example as in measurements of specific metabolites. However, as explained above, the main problem in most clinical examinations is the chemical shift of the fat portion relative to the typically excited water, such that the method is advantageously used to avoid artifacts occurring due to the chemical shift of water and fat. This means that water and fat are preferably, respectively to be understood as first and second material in the sense of the invention. In the following, these materials are therefore always used as an example without limiting the invention to this embodiment.

If the materials and their chemical shift are known, a relative position shift of the measurement slices of the first and second materials relative to one another (which relative position shift is due to this chemical shift) can advantageously be determined calculated automatically for a specific slice measurement sequence or series of slice measurement sequences. An additional input value is the employed pulse bandwidth of the slice excitation radio-frequency pulses within the slice measurement sequence or slice measurement sequences. A suitable formation of combination slice acquisitions can then take place based on this precalculated position shift, such that the position shift is corrected again.

In principle, within the scope of the invention all series of slice measurement sequences can be used that allow a separation of the two materials (thus for example a fat/water separation). For example, series of slice measurement sequences can be used in which a separate excitation of the first material and a separate excitation of the second material respectively take place with relative low bandwidth. A distinct spatial displacement of the slices is in fact thereby achieved. However, this is not a problem since the slice displacement is compensated according to the invention.

As mentioned, however, the slice measurement sequences are preferably designed so that they each allow a separation of the first material from the second material within the respective slice measurement sequence, and the position of the measurement slice with measurement data for the first material is thereby spatially shifted relative to the position of a measurement slice with measurement data for the second material (i.e. in the same slice measurement sequence). In the calculation of the combination slice exposures, corresponding measurement data from different slice measurement sequences (advantageously slice measurement sequences in immediate succession) are then combined with one another. Such a slice measurement sequence is, for example, known as the Dixon sequence, in which multiple echoes are acquired within a sequence after a single excitation, wherein the image data of the different materials are shifted in terms of their phase. Such a Dixon sequence is, for example, described in H. Yu et al.: "Implementation and Noise Analysis of Chemical Shift Correction for Fast Spin Echo Dixon Imaging" in Proc. Intl. Soc. Mag. Reson. Med. 11 (2004), 2686, a Dixon sequence is used in order to achieve a correction of the chemical shift within an image plane via multiplication of the k-space lines with a specific phase term.

An advantage of such a series of slice measurement sequences, in which the measurement data for the first material and the second material are measured simultaneously within a slice measurement sequence, is that these sequences save more time than a separate excitation of the two materials. An additional advantage of the Dixon method for separation of the respective signal content of multiple materials is that it is more robust—with regard to inhomogeneities of the basic magnetic field—than methods that, for example, are based on spectral excitation or suppression of various materials via radio-frequency pulses.

Since the raw data acquired for a measurement slice already include all information about the image, it is possible in principle to link these raw data in a suitable manner and to subsequently generate the combination slice exposures made from these combined raw data. However, the combination of the measurement data preferably takes place only at the image data level, meaning that image data for the appertaining measurement slices are initially generated from the raw data for the individual measurement slices, and these individual measurement slices are then combined. The combination of the measurement data particularly preferably is an addition of image data of the first and second material that are spatially arranged with precise position relative to one another (at least within a predetermined degree of tolerance), which means it is ensured that the image data for the two materials are superimposed on one another with precise position (within the degree of tolerance) in the combination slice exposures. A weighted addition is also possible, wherein a negative algebraic sign is also conceivable in the weighting factors (thus a subtraction).

There are various possibilities for the generation of the combination slice exposures.

In a preferred variant, the series of slice measurement sequences is selected such that the position of a measurement slice with measurement data for the first material from a first slice measurement sequence and the position of a measurement slice with measurement data for the second material from a time-shifted, second slice measurement sequence coincide, at least within a predetermined degree of tolerance. This method is also possible when both measurement data for the first material and measurement data for the second material are generated within a measurement slice. For this purpose, a spatial shift (caused by the chemical shift) of the position of the measurement slices of the first material and second material relative to one another is advantageously determined beforehand and taken into account in the design of the slice measurement sequences. For example, a first measurement slice for water and a first measurement slice for fat that was spatially shifted relative to said first measurement slice for water can be generated in a first slice measurement sequence. In an immediately following slice measurement sequence, a second measurement slice is then generated for water and a spatially shifted second measurement slice is generated for fat, wherein it is ensured that this second measurement slice for water coincides, in terms of its position, within the first measurement slice for the fat from the first slice measurement sequence (within the predetermined degree of tolerance). The measurement data for the water from the second slice measurement sequence can then consequently be directly combined with the measurement data for the fat from the first slice measurement sequence (for example, the image data can simply be superimposed). The measurement data for water from the second slice measurement sequence can then be combined in a corresponding manner with the measurement data for the fat from the third slice measurement sequence etc.

For this purpose, the series of slice measurement sequences can be automatically calculated on the basis of control specifications before a measurement session (i.e. before a complete acquisition of the stack of measurement slices), wherein these control specifications can be predetermined by the operator and/or are established in a measurement protocol. The control specifications can thereby advantageously include at least one of the following measurement parameters:

a slice thickness of a measurement slice or, respectively, the slice thicknesses of all desired measurement slices, a position interval of measurement slices of successive slice measurement sequences, meaning the slice interval from the middle point of a measurement slice to the middle point of the subsequent measurement slice, a pulse length and/or pulse shape (temporal amplitude curve) of a slice selection radio-frequency pulse of a slice measurement sequence, wherein the minimum and/or the maximum or even an exactly precise pulse length can be predetermined, for example. The pulse lengths/shapes of all slice measurement sequences are thereby advantageously predetermined.

The pulse bandwidths of the radio-frequency pulses of the slice measurement sequence can be calculated from all of these data so that, as previously described, the measurement slices of the different materials from the different slice measurement sequences (advantageously directly successive slice measurement sequences) come to match one another.

In a further preferred variant, a spatial correction is implemented based on a determined position shift before and/or upon formation of the combination slice exposures, at least for the measurement data of one of the materials, meaning that the measurement data are spatially shifted in a suitable manner.

Such a correction is advantageously possible by generating, for at least one of the materials, synthetic measurement data for a virtual slice from measurement data that are spatially shifted counter to one another (normally spaced apart from one another) and that were generated with different, time-shifted slice measurements of the series of slice measurement sequences. "Synthetic measurement data" means artificially generated data that correspond, with regard to their format, to real measurement data, but that are generated by a combination of the measurement data from the real measurement slices. "Measurement data" thus can be generated for a slice—the "virtual slice"—that advantageously lies at the arbitrary desired position between the measurement slices from which the real measurement data originate that were used for generation of the synthetic measurement data. The synthetic measurement data can be generated by an interpolation of the measurement data from the real measurement slices.

The position of a virtual slice with the synthetic measurement data for a material can thereby advantageously be selected so that it coincides with the position of a measurement slice with measurement data of the other material within a predetermined degree of tolerance. It is then relatively simple to combine the synthetic measurement data from the virtual measurement slice of the one material with the measurement data of the other material from the real measurement slice at a matching position, in order to thus obtain desired combination slice exposures.

Independently of whether it has already been ensured in the generation of the measurement slices that these measurement slices of the different materials come to be situated in a matching manner, or whether a correction of a material takes place via an interpolation, for example, the number of measurement slices is chosen to be greater than the number of combination slice exposures. In fact, it would in principle also be possible to generate as many combination slice exposures as measurement slices that were measured in total for each of the materials. However, in a border region of the slice stack it would then be necessary to generate synthetic measurement data outside of the slice stack (for example via an extrapolation method), which naturally is linked with greater uncertainty than an interpolation method or another correction method that can resort to information from neighboring measurement slices on both sides in the slice stack.

As explained above, the basic magnetic field should be optimally homogeneous. However, for technical reasons it is sometimes the case that inhomogeneities in the basic magnetic field (also designated as a $B_0$ field distortion) can occur in border regions of the magnetic resonance tomograph. Subjects with different magnetic susceptibilities represent another source of inhomogeneities. For example, local field changes are thus inevitable in the transition from the body tissue to the surrounding air. Local field inhomogeneities cause an additional frequency offset, and therefore an additional spatial signal displacement that can be taken into account in the image reconstruction given known size of the offsets. Therefore, in a preferred variant it is also possible to take into account such inhomogeneities of the basic magnetic field—in particular given correction of the measurement data, for example given a determination of a suitable slice measurement sequence—and implement the corrections accordingly or, respectively, design the slice measurement sequences accordingly in order to compensate for these inhomogeneities again.

For example, the $B_0$-field distortion can be measured in advance for the appertaining magnetic resonance system and be stored in a memory. However, in principle it is also possible to determine these $B_0$ field distortions individually (including the local field changes caused by the subject introduced into the magnet) via a measurement of the $B_0$ field distribution directly before the actual usable measurement in an adjustment measurement, and to then use the data for the method according to the invention. Furthermore, it is possible to determine changes in the signal phase (field changes), for example, via analysis of the measurement data themselves.

However, the effect of the chemical shift produces a false spatial association ("shift") of the signal not only in the slice direction (typically the z-axis) but also in the plane in the direction of the frequency coding (for example the x-axis). Since magnitude and direction of the shift along the direction of the frequency coding are established (and therefore known) by the sequence parameters, this effect can also be taken into account given calculation of the combined slices. For this purpose, the slice of the second material must be shifted accordingly only along the direction of the frequency coding given combination with the slice of the first material. The chemical shift can thus be compensated completely (i.e. in both directions) with this method.

DESCRIPTION OF THE PREFERRED EMBODIMENTS

Figure 1:
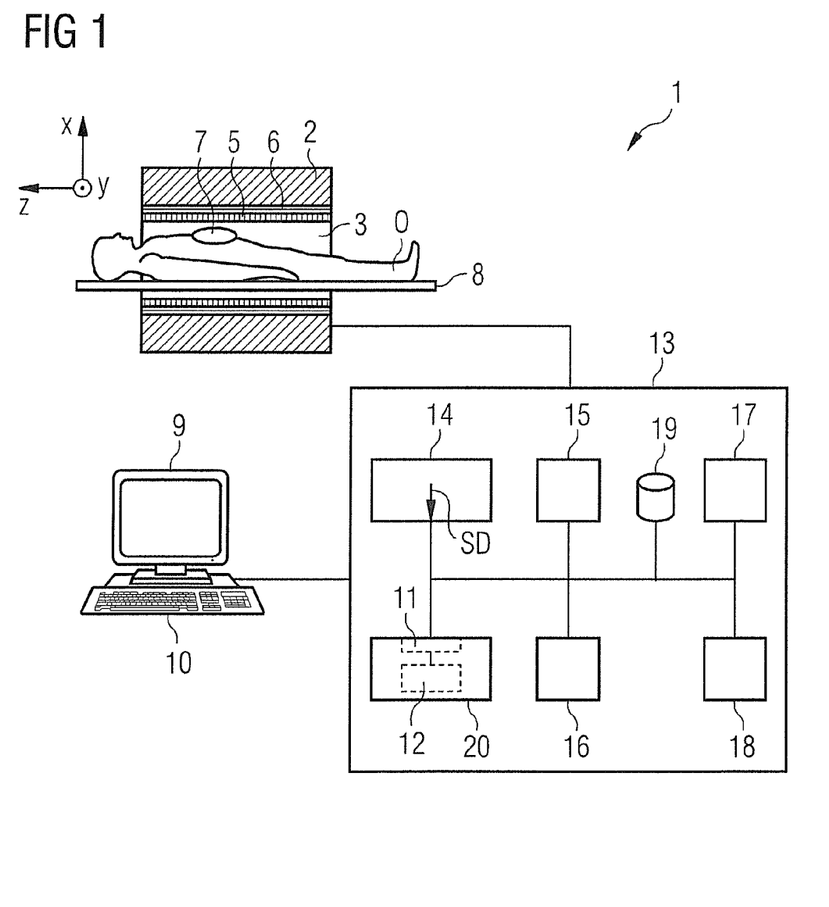
FIG. 1 is a schematic illustration of a magnetic resonance system according to an exemplary embodiment of the invention.

A magnetic resonance system 1 according to the invention (called an "MR system" for short in the following) is schematically shown in FIG. 1. The MR system 1 includes the actual magnetic resonance scanner (data acquisition unit) 2 with an examination space 3 (patient tunnel) into which an examination subject O (here a patient) can be moved on a driven bed 8.

The magnetic resonance scanner 2 is typically equipped with a basic field magnet system 4, a gradient system 6 as well as an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 is formed as local coils (symbolized by only a single local coil in FIG. 1) to be arranged on the patient or test subject. In principle, however, the whole-body coil can also be used as an RF reception antenna system, and the local coils (as an RF ran system) can respectively be switched into different operating modes. The basic field magnet system 4 here is designed in a typical manner so that it generates a basic magnetic field in the longitudinal direction of the patient, i.e. along the longitudinal axis of the magnetic resonance scanner 2 that proceeds in the z-direction. The gradient system 6 typically includes individually controllable gradient coils in order to be able to switch (activate) gradients in the x-direction, y-direction or z-direction independently of one another.

In the following exemplary embodiments, it is assumed that a slice stack is acquired in a stack direction proceeding in the z-direction, meaning that all measurement slices lie in parallel in the x/y-plane. The individual slices can consequently be selected for MR data acquisition therefrom by simultaneous application of a slice selection gradient Gz in the z-direction upon emission of a radio-frequency excitation pulse. However, the inventive principle is not limited to such a slice stack arranged along a z-axis. It can also be applied given slice stacks in an arbitrary arrangement.

The MR system shown in FIG. 1 is a whole-body system with a patient tunnel into which a patient can be completely introduced. However, in principle the invention can also be used at other MR systems, for example with a laterally open, C-shaped housing, as well as in smaller magnetic resonance scanners in which only one body part can be positioned, for example.

Furthermore, the MR system 1 has a central control device 13 that is used to control the MR system 1. This central control device 13 includes a sequence control unit 14 for measurement sequence control. With this sequence control unit 14, the series of radio-frequency pulses (RF pulses) and gradient pulses can be controlled depending on a selected slice measurement sequence or, respectively, a series of multiple slice measurement sequences to acquire multiple slices within a measurement session. For example, such a series of slice measurement sequences can be predetermined within a measurement or control protocol. Different control protocols for different measurements or measurement sessions are typically stored in a memory 19 and can be selected by and operator (and possibly modified as necessary) and then be used to implement the measurement.

To output the individual RF pulses, the central control device 13 has a radio-frequency transmission device 15 that generates and amplifies the RF pulses and feeds them into the RF transmission antenna system 5 via a suitable interface (not shown in detail). To control the gradient coils of the gradient system 6, the control device 13 has a gradient system interface 16. The sequence control unit 14 communicates in a suitable manner (for example via emission of sequence control data SD) with the radio-frequency transmission device 15 and the gradient system interface 16 to emit the slice measurement sequences. Moreover, the control device 13 has a radio-frequency reception device 17 (likewise communicating with the sequence control unit 14 in a suitable manner) in order to acquire magnetic resonance signals (i.e. raw data) for the individual measurement slices, which magnetic resonance signals are received in a coordinated manner from the RF transmission antenna system 7 within the scope of the slice measurement sequences.

Here a reconstruction unit 18 receives the acquired raw data and reconstructs magnetic resonance image data therefrom for the measurement slices. For example, the image data can then be stored in a memory 19. Moreover, the image data as measurement data of the individual measurement slices can be further processed in a measurement data processing unit 20 in a manner according to the invention. The measurement data processing unit 20 here has a measurement data interface 11 to accept the measurement data. In a measurement data combination unit 12, the combination slice exposures are then generated on the basis of the measurement data as is explained again using FIGS. 3 and 4.

These combination slice exposures can be emitted again—for example be stored in the memory 19—via the measurement data interface 11. Alternatively, the measurement data processing unit 20 (in particular the measurement data combination unit 12) can be integrated into the reconstruction unit 18 or can be externally connected to the central control device 13 via a network or the like.

Operation of the central control device 13 can take place via a terminal with an input unit 10 and a display unit 9, via which the entire MR system 1 can thus also be operated by an operator. MR images can also be displayed at the display unit 9, and measurements can be planned and started by means of the input unit 10 (possibly in combination with the display unit 9), and in particular suitable control protocols with suitable control protocols can be selected (and possibly modified) with suitable series of slice measurement sequences as explained above.

The MR system 1 according to the invention, and in particular the control device 13, can have a number of additional components that are not shown in detail but are typically present at such systems, for example a network interface in order to connect the entire system with a network and be able to exchange raw data and/or image data or, respectively, parameter maps, but also additional data (for example patient-relevant data or control protocols).

The manner by which suitable raw data are acquired by radiation of RF pulses and the generation of gradient fields, and MR images are reconstructed from the raw data, is known to those skilled in the art and thus need not be explained in detail herein. The most varied slice measurement sequences (for example TSE measurement sequences or Dixon measurement sequences) are likewise fundamentally known to those skilled in the art.

Figure 2:
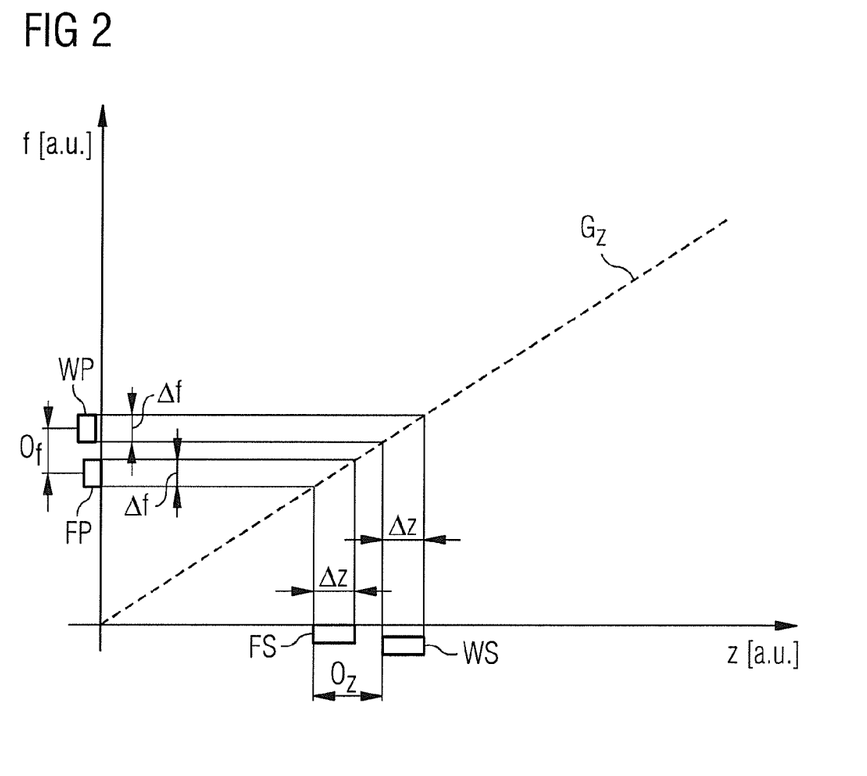
FIG. 2 schematically shows the dependency of the slice width and the slice interval on the pulse bandwidth of a slice selection radio-frequency pulse.

The relationship between the bandwidth Δf a radio-frequency pulse emitted for slice selection, the strength or amplitude of the applied slice selection gradient field Gz (and the slice thickness Δz resulting from this) and the slice interface $O_z$, is explained again in connection with FIG. 2.

In FIG. 2 the frequency f (in arbitrary units) is plotted over the position z (in arbitrary units). The current gradient strength Gz is likewise drawn as a straight line. The slope of these straight lines is correlated with the strength (i.e. the amplitude) of the gradient pulse.

Here the frequency bandwidth Δf of a slice selection excitation pulse is shown along the frequency axis in the form of two blocks WP, FP. Here—as is generally the case—the half width of the frequency range of the excitation pulse is viewed as a frequency bandwidth. The upper block WP lies in the range of the desired Larmor frequency of water, meaning that it represents the excitation bandwidth of water. The lower block FP represents the same frequency bandwidth Δf around the Larmor frequency of fat, thus represents the excitation bandwidth of fat, wherein the Larmor frequency of fat is (however) lower by 3.5 ppm than the Larmor frequency of water. This difference in the Larmor frequency or, respectively, excitation frequency here is also designated as a frequency offset $O_F$.

At a given frequency bandwidth Δf, and at a given gradient strength Gz (=amplitude of the slice selection gradient), the thickness Δz of the selected slice is provided by the following equation:

$$\Delta z = \frac{2\pi \cdot \Delta f}{\gamma \cdot Gz} \qquad (1)$$

wherein γ is the gyromagnetic moment for protons, i.e. a constant.

In FIG. 2 it is clear how a specific bandwidth Δ at a given gradient strength Gz leads to a specific slice thickness Δz. Shown here on the z-axis are the width and position of the excited water slice ES and the width and position of the excited fat slice FS. The thicknesses of the slices are identical for both water and fat, corresponding to the frequency bandwidths Δf. However, here it is clearly apparent that—due to the frequency offset $O_f$—the water slice WS has shifted relative to the fat slice FS by a specific interval $O_z$ (called position offset $O_z$ in the following). This position offset $O_z$ can be described by the following equation, analogous to Equation 1:

$$O_z = \frac{2\pi \cdot O_f}{\gamma \cdot Gz} \qquad (2)$$

$O_f$ is again the fixed frequency offset $O_f$ of 3.5 ppm for water and fat, relative to the basic frequency of protons in a given magnetic field. It is thereby clear that the spatial position offset $O_z$ depends only on the gradient strength Gz and the strength of the static basic magnetic field. Whether the water slice WS and the fat slice FS thus still overlap and show information from the same spatial region thus moreover depends on the selected gradient strength Gz and the magnetic field strength of the pulse bandwidth Δz of the slice selection radio-frequency pulse as well. If—as is the case here—a relatively narrow pulse bandwidth Δf is selected, the magnetic resonance signals of the adipose material that are generated upon emission of a specific slice selection radio-frequency pulse with a defined bandwidth Δf and a defined frequency come from a spatially completely different slice than the magnetic resonance signals of the water signal, which leads to corresponding artifacts.

In order to counteract this problem, it has always previously been attempted to acquire the raw data using an optimally large bandwidth, which (however) runs contrary to the efforts for an optimally low SAR exposure. According to the invention, it is therefore now proposed to deliberately acquire raw data with a separate series of slice measurement sequences, and to only subsequently combine the measurement data with precise positioning in a suitable manner or, respectively, (as described in the following exemplary embodiments) to superimpose the reconstructed image data from the different measurement slices with precise position.

Figure 3:
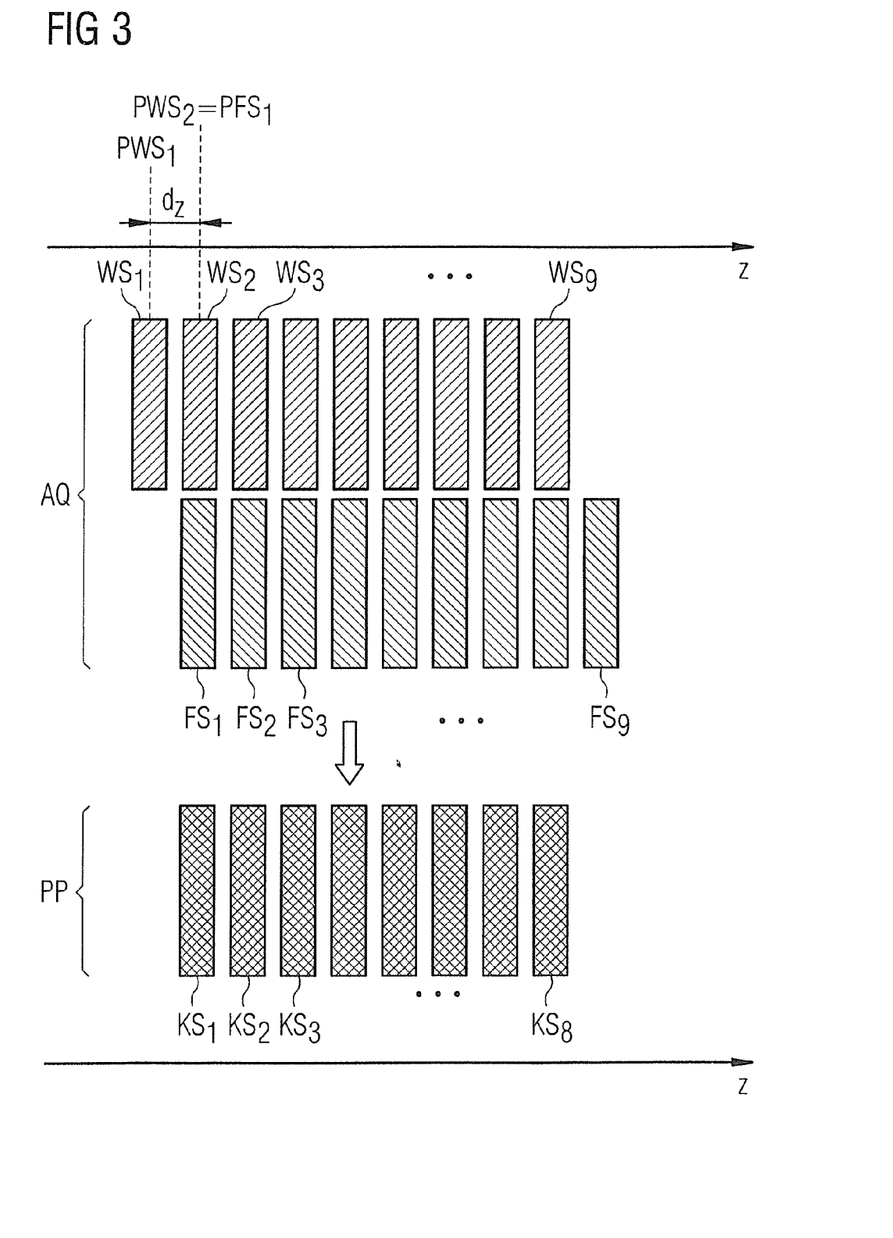
FIG. 3 schematically shows the combination of measurement data of different materials from different measurement slices according to a first embodiment of the method according to the invention.

A first exemplary embodiment in this regard is schematically shown in FIG. 3. It should be noted that the arbitrarily selected z-direction is rotated in FIGS. 3 and 4 relative to FIG. 2. Schematically shown are multiple measurement slices $WS_1$, $WS_2$, $WS_3$, ..., $WS_9$ for water and multiple measurement slices $FS_1$, $FS_2$, $FS_3$, ..., $FS_9$ for fat, which measurement slices were acquired with a Dixon measurement sequence within the scope of an acquisition step AQ. The slices for a material are thereby respectively shown next to one another in the z-direction. The measurement slices $WS_1$, $WS_2$, $WS_3$, ..., $WS_9$ for water are shown in the uppermost row, and the measurement slices $FS_1$, $FS_2$, $FS_3$, ..., $FS_9$ for fat are shown in the row below that. The number of the slices $WS_1$, $WS_2$, $WS_3$, ..., $WS_9$ for water and the slices $FS_1$, $FS_2$, $FS_3$, ..., $FS_9$ for fat or the indexing takes place here so that the slices with the same index were acquired simultaneously in a slice measurement sequence in that two echoes—one echo for water and one echo for fat—were generated.

The parameters of the Dixon measurement sequence were set so that the slice interface $d_z$ between two successively measured water slices $WS_1$, $WS_2$, $WS_3$, ..., $WS_9$ and between two successive fat slices $FS_1$, $FS_2$, $FS_3$, ..., $FS_9$ corresponds precisely to the position offset $O_z$ between a measurement slice $WS_1$, $WS_2$, $WS_3$, ..., $WS_9$ for water and a measurement slice $FS_1$, $FS_2$, $FS_3$, ..., $FS_9$ for fat that is acquired within the same slice measurement sequence. This is shown using the first two slices $WS_1$, $WS_2$, $FS_1$, $FS_2$. The first measurement slice $WS_1$ for water here is situated at a position $PWS_1$. Due to the position offset $O_z$, the measurement slice $FS_1$ for fat that is acquired in this slice measurement sequence is shifted by a distance $d_z$. With corresponding adjustment of the Dixon sequence (namely by the matching adjustment of the slice interval of the successive slice measurement sequences) it is ensured that the slice interval $d_z$ of the successive measurement slice $WS_2$ for water from this second slice measurement sequence corresponds exactly to the position offset $O_z$, such that the position $PWS_2$ of the second measurement slice $WS_2$ for water corresponds exactly to the position PFS of the first measurement slice $FS_1$ for fat. This slice interval $d_z$ is also maintained in all additional measurement slices or, respectively, slice measurement sequences, such that the fat slice of a slice measurement sequence always coincides with precise position with the water layer of a subsequent slice measurement sequence.

The measurement data for water and fat that are determined separately in such a manner are then combined in a post-processing step PP so that the measurement data that are situated atop one another with precise positioning are combined into combination slice exposures $KS_1$, $KS_2$, $KS_3$, ..., $KS_8$. This is possible by a simple, pixel-by-pixel addition of the image data.

In this way, slice exposures are generated that include both water signal and fat signal which are free of artifacts caused by the chemical shift between water and fat. This method can thereby be implemented given an arbitrary bandwidth of the excitation pulses so that SAR-reduced measurements are also possible even in magnetic resonance tomographs with very high magnetic field of, for example, 7 Tesla. The slice interval to be set for the Dixon sequence can be calculated very simply (as explained above using FIG. 2) given a known slice-selection gradient strength Gz and known frequency bandwidth Δt or the position offset $O_z$ is calculated and the slice interval $d_z$ is selected accordingly.

As is apparent from FIG. 3, more slice measurement sequences are advantageously implemented than combination slice exposures $KS_1$, $KS_2$, $KS_3$, ..., $KS_8$ are generated afterward, since a measurement slice at the edges can respectively not be used, namely the first water measurement slice $WS_1$ and the last fat measurement slice $FS_9$.

Figure 4:
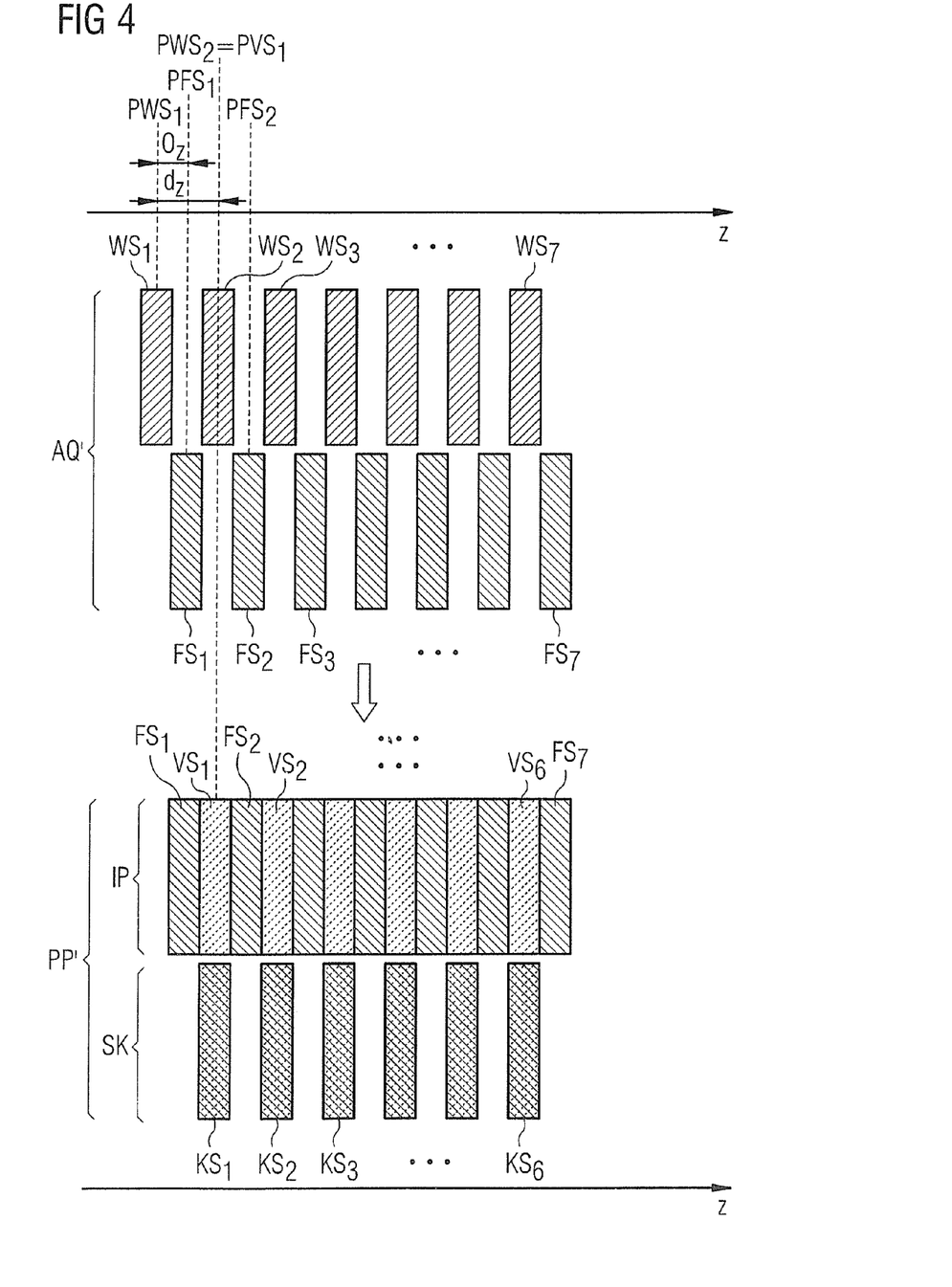
FIG. 4 schematically shows the combination of measurement data of different materials from different measurement slices according to a second embodiment of the method according to the invention.

FIG. 4 shows an alternative method embodiment that can be used when the interval between two successive measurement slices $WS_1$, $WS_2$, $WS_3$, ..., $WS_9$, $FS_1$, $FS_2$, $FS_3$, ..., $FS_9$ of one of the materials does not coincide with the position offset $O_z$, for example because a very dense coverage of the ROI is not required, and therefore larger slice intervals should be selected.

In the exemplary embodiment shown in FIG. 4, a measurement with a Dixon sequence within an acquisition slice AQ' initially takes place again. The slice interval $d_z$ is hereby chosen to be twice as large as the position offset $O_z$, which leads to the situation that the position $PFS_1$ of a measurement slice $FS_1$ for fat lies precisely between the positions $PWS_1$, $PWS_2$ of two successive measurement slices $WS_1$, $WS_2$ for water.

Nevertheless, in order to be able to combine the measurement data in a positionally precise manner, in a post-processing step PP' respective synthetic measurement data in virtual measurement slices $VS1$, $VS_2$, ..., $VS_6$ are initially generated from the measurement data of the measurement slices $FS_1$, $FS_2$, ..., $FS_7$ for the fat in a first interpolation step 1P. These synthetic measurement data are measurement data that are interpolated from the real measurement data of the two adjacent fat measurement slice $FS_1$, $FS_2$, ..., $FS_7$. The spatial position of such a virtual slice $VS_1$ for fat is selected so that it corresponds precisely to the position $PWS_2$ of a measurement slice $WS_2$ for water, as this is shown at the top in FIG. 4 for the second water slice $WS_2$ and the first virtual measurement slice $VS_1$ for fat.

In a further combination step SK, the synthetic measurement data from these virtual measurement slices $VS_1$, $VS_2$, ..., $VS_6$ for fat are then superimposed with the real measurement data from the corresponding, positionally correlated measurement slices $WS_2$, $WS_3$, ..., $WS_7$ for water in order to thus generate the desired combination slice images $KS_1$, $KS_2$, ..., $KS_6$. This can again take place via a per-pixel addition.

Slice images that are not fat-suppressed can thus also be generated relatively simply with this second method, without generating artifacts caused by a chemical shift.

Figure 5:
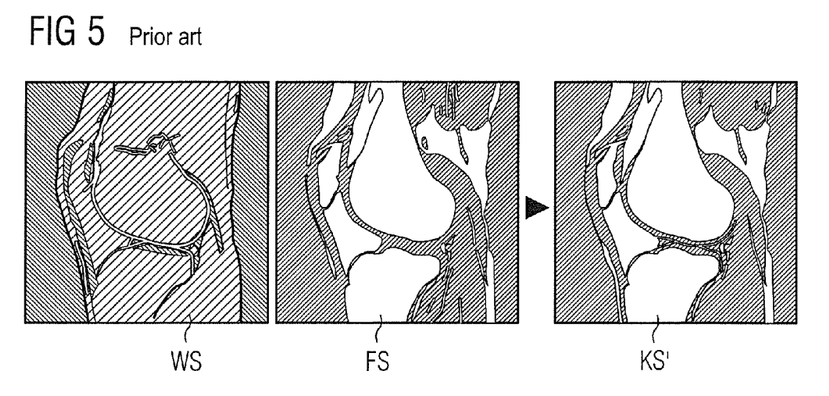
FIG. 5 schematically shows an example of separate slices for water and fat that are acquired with a Dixon sequence, as well as their combination into one slice exposure, wherein the combined image corresponds to the result of a conventional measurement in which water and fat are superimposed, and wherein it is clear that the water proportion and fat proportion are incorrectly spatially registered.
Figure 6:
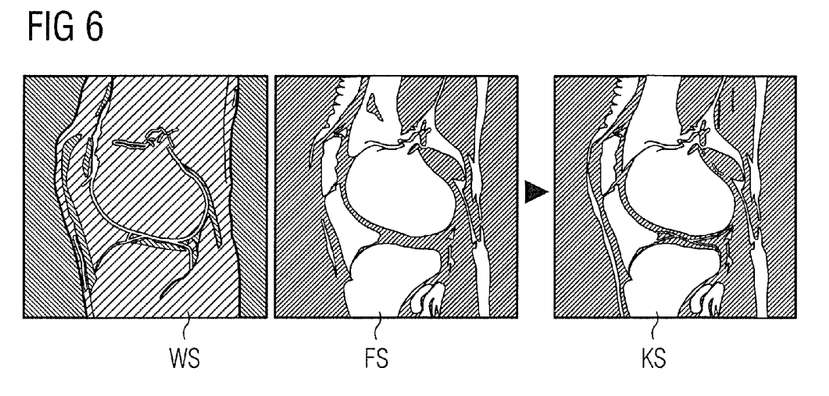
FIG. 6 shows the example of the separate slices acquired with a Dixon sequence for water and fat according to FIG. 5, as well as their combination into a slice exposure in the method according to the invention.

This advantage of the method is shown again using images of a test measurement in connection with FIGS. 5 and 6.

In the far left image and in the middle image, FIG. 5 shows (schematic) slice exposures through a knee which were acquired with a 2-point Dixon TSE sequence in a 3-Tesla magnetic resonance tomograph. An excitation radio-frequency bandwidth of 350 Hz was hereby used. The slice thickness was 4 mm and the slice interval was 0.5 mm. Given the selected bandwidth of 350 Hz, the position offset due to the chemical shift was already 4.5 mm, which lead to the situation that the actual spatial position of the fat signal no longer coincided with the spatial position of the water signal from the same slice measurement sequence (as this is assumed in the previous processing of the measurement data). The far left image thereby shows the third slice of the water signal WS, and the middle image FS shows the third slice of the fat signal. If these image data are now superimposed in a typical manner to form a combination image, the combination slice exposure KS' situated at the far right is thus obtained, in which combination slice exposure KS' artifacts due to the spatial displacement of the fat signal and the water signal clearly form, which means that the shown structure no longer coincides with the real structure in the knee. The artifact-affected combination image KS' furthermore corresponds to the result of a conventional TSE sequence (without Dixon method) as it is generally, typically used for clinical imaging without fat saturation.

In contrast to this, FIG. 6 shows (schematic) images of the method according to the invention. The far left image here corresponds to the third slice of the water signal, and the middle image corresponds to the second slice of the fat signal.

When if these image data from two successive Dixon sequences (which image data are superimposed with precise positioning) are now combined with one another, the combination slice exposure KS (far right) is generated which is free of artifacts in the sense that both water and fat originate from the same spatial position.

The exemplary embodiments described in the preceding thus very clearly show how images that are not fat-suppressed can be generated with only slight effort with the aid of the method according to the invention, which images are free of artifacts due to the chemical shift between fat and water. In particular, the exemplary embodiments show that, even given magnetic resonance systems of 3 Tesla or more, it is possible without additional measures to drive turbo spin echo sequences that are not fat-suppressed with reduced bandwidth (=reduced SAR) and to use these sequences for a routine imaging.

Finally, it is noted again that the methods and designs described in detail in the preceding are only exemplary embodiments, and the described basic principles can be modified by those skilled in the art without departing from the scope of the invention. As already mentioned, it is possible to directly combine the raw data instead of the reconstructed image data for the different slices, and only then to implement an image data reconstruction on the basis of the combined raw data.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method to generate a slice exposure of an examination subject by a magnetic resonance imaging, comprising:
    operating a magnetic resonance data acquisition unit to acquire magnetic resonance measurement data for a stack of measurement slices through an examination subject with a series of slice measurement sequences configured to allow separation of a first material in the examination subject from a second material in the examination subject, said second material having a defined chemical shift with respect to the first material, with a position of a measurement slice containing magnetic resonance measurement data for said first material being spatially shifted relative to a position of a measurement slice containing magnetic resonance measurement data for the second material;
    providing said magnetic resonance measurement data acquired in said series of slice measurement sequences to a processor and, in said processor, forming a combination of slice exposures in which the first and second materials are shown by combining magnetic resonance measurement data of said first material from at least a first of said slice measurement sequences with magnetic resonance measurement data of said second material from at least a second of said slice measurement sequences, with image data respectively for said first and second materials in said combination slice exposures being spatially located with a positioning relative to each other that is within a predetermined range of tolerance; and
    in said processor, generating a data file that includes said combination slice exposures, and making said data file available at an output of said processor in electronic form.

2. A method as claimed in claim 1 comprising acquiring said magnetic resonance measurement data for said stack of measurement slices by operating said magnetic resonance data acquisition unit to radiate a radio frequency pulse in each slice measurement sequence that determines said position shift of the respective measurement slices containing said first and second materials, and using said position shift that is determined by said radio frequency pulse to generate, in said processor, said combination slice exposures.

3. A method as claimed in claim 1 comprising operating said magnetic resonance data acquisition unit to acquire said measurement data for said stack of measurement slices with said series of slice measurement sequences configured to respectively allow, in each of said slice measurement sequences in said series, said separation of said first material from said second material, and wherein, in each of said respective slice measurement sequences in said series, the position of said measurement slice containing magnetic resonance measurement data for said first material is shifted from a measurement slice containing said magnetic resonance measurement data for said second material.

4. A method as claimed in claim 1 comprising, in said processor, generating image data respectively for said magnetic resonance measurement data from said first material and from said magnetic resonance measurement data for said second material, and generating said combination slice exposures using said image data.

5. A method as claimed in claim 1 comprising operating said magnetic resonance data acquisition unit with said series of slice measurement sequences configured to cause said position of a measurement slice containing said magnetic resonance measurement data for said first material in a first of said slice measurement sequences to coincide with a position of a measurement slice containing said magnetic resonance measurement data for said second material in a second of said slice measurement sequences, within a further predetermined degree of tolerance.

6. A method as claimed in claim 5 comprising operating said magnetic resonance data acquisition unit with control specifications to generate said series of slice measurement sequences, and selecting said control specifications from the group consisting of setting a slice thickness of respective measurement slices, setting a position interval between measurement slices in successive slice measurement sequences, setting a precise pulse length of a slice-selection radio frequency pulse in each slice measurement sequence, setting a minimum of a pulse length of a slice-selection radio frequency pulse of a slice measurement sequence, setting a maximum of a pulse length of a slice-selection radio frequency pulse of a slice measurement sequence, setting a pulse shape with a minimum bandwidth of a slice-selection radio frequency pulse of a slice measurement sequence, setting a pulse shape with a maximum bandwidth of a slice-selection radio frequency pulse of a slice measurement sequence, and setting a pulse shape with a precise bandwidth of a slice-selection radio frequency pulse of a slice measurement sequence.

7. A method as claimed in claim 1 comprising, in said processor, implementing a spatial correction based on said position shift, for the magnetic resonance measurement data of at least one of said first and second materials, at a time selected from the group consisting of the four forming said combination slice exposures and during formation of said combination slice exposures.

8. A method as claimed in claim 7 comprising, in said processor, generating, for at least one of said first and second materials, synthesized measurement data for a virtual slice that originate from respective measurement slices that are spatially shifted counter to one another and that were generated with different slice measurement sequences of said series of slice measurement sequences.

9. A method as claimed in claim 8 comprising generating said synthesized measurement data by interpolation of measurement data from said measurement slices that are spatially shifted counter to one another.

10. A method as claimed in claim 8 comprising determining a position of said virtual slice for said at least one of said first and second materials so as to coincide with a position of a measurement slice containing said MR measurement data of the other of said at least one of said first and second materials, within a further predetermined range of tolerance.

11. A method as claimed in claim 1 comprising operating said magnetic resonance data acquisition unit and said processor to cause a number of said measurement slices to be larger than a number of said combination slice exposures.

12. A method as claimed in claim 1 wherein operating said magnetic resonance data acquisition unit includes generating a basic magnetic field in said magnetic resonance data acquisition unit, said basic magnetic field exhibiting a field inhomogeneity, and comprising, in said processor, taking said field inhomogeneity into account when forming said combination slice exposures.

13. A magnetic resonance data processing unit to generate a slice exposure of an examination subject by a magnetic resonance imaging, comprising:

a processor;

said processor having an input that receives magnetic resonance measurement data for a stack of measurement slices through an examination subject acquired with a series of slice measurement sequences configured to allow separation of a first material in the examination subject from a second material in the examination subject, said second material having a defined chemical shift with respect to the first material, with a position of a measurement slice containing magnetic resonance measurement data for said first material being spatially shifted relative to a position of a measurement slice containing magnetic resonance measurement data for the second material;

in said processor, being configured to form a combination of slice exposures in which the first and second materials are shown by combining magnetic resonance measurement data of said first material from at least a first of said slice measurement sequences with magnetic resonance measurement data of said second material from at least a second of said slice measurement sequences, with image data respectively for said first and second materials in said combination slice exposures being spatially located with a positioning relative to each other that is within a predetermined range of tolerance;

said processor being configured to generate a data file that includes said combination slice exposures; and said processor having an output at which said data file is available in electronic form.

14. A magnetic resonance apparatus to generate a slice exposure of an examination subject by a magnetic resonance imaging, comprising:

a magnetic resonance data acquisition unit;

a control unit configured to operate said magnetic resonance data acquisition unit to acquire magnetic resonance measurement data for a stack of measurement slices through an examination subject with a series of slice measurement sequences configured to allow separation of a first material in the examination subject from a second material in the examination subject, said second material having a defined chemical shift with respect to the first material, with a position of a measurement slice containing magnetic resonance measurement data for said first material being spatially shifted relative to a position of a measurement slice containing magnetic resonance measurement data for the second material;

a processor provided with said magnetic resonance measurement data acquired in said series of slice measurement sequences to a processor, said processor being configured form a combination of slice exposures in which the first and second materials are shown by combining magnetic resonance measurement data of said first material from at least a first of said slice measurement sequences with magnetic resonance measurement data of said second material from at least a second of said slice measurement sequences, with image data respectively for said first and second materials in said combination slice exposures being spatially located with a positioning relative to each other that is within a predetermined range of tolerance; and said processor being configured to generate a data file that includes said combination slice exposures, and to make said data file available at an output of said processor in electronic form.

\* \* \* \* \*